United States Patent [19]

Scherr

[11] Patent Number: 5,718,916
[45] Date of Patent: Feb. 17, 1998

[54] ALGINATE FOAM PRODUCTS

[76] Inventor: George H. Scherr, P.O. Box 134, Park Forest, Ill. 60466

[21] Appl. No.: 792,374

[22] Filed: Feb. 3, 1997

[51] Int. Cl.$^6$ .................................................. A61L 15/00
[52] U.S. Cl. ........................... 424/445; 424/400; 424/484
[58] Field of Search .......................... 424/44, 445, 443, 424/619, 715, 722, 43, DIG. 13, 484, 400; 604/85, 304; 523/111, 113

[56] References Cited

U.S. PATENT DOCUMENTS

| | | | |
|---|---|---|---|
| 3,653,383 | 4/1972 | Wise | 128/296 |
| 4,948,575 | 8/1990 | Cole et al. | 424/44 |
| 5,089,606 | 2/1992 | Cole et al. | 536/54 |
| 5,409,703 | 4/1995 | McAnalley et al. | 424/435 |
| 5,470,576 | 11/1995 | Patel | 424/445 |

Primary Examiner—Thurman K. Page
Assistant Examiner—Kathryne E. Shelborne

[57] ABSTRACT

A composition sodium alginate which is capable of being formed into an insoluble alginate salt in a mold or dish which insoluble alginate salt may be frozen and lyophilized resulting in an alginate foam product which has utility in wound management as a dressing, in surgical, and implant procedures. The insoluble alginate salt thus formed may also be prepared as a coercive mixture or covalent-link mixture with insolubilizing chemical agents which thus provide a product having utility as a medical dressing, in surgical, and implant procedures, which can retain their integrity in or on tissues over extended periods of time and a method of making the same.

22 Claims, No Drawings

ALGINATE FOAM PRODUCTS

The present invention relates to novel alginate compositions and methods of making same, which can be utilized in the medical and veterinary fields. More specifically, the invention relates to novel compositions of alginate which can be prepared in the form of a sponge-like or foam product which, according to the composition, may be utilized in the preparation of various bandages or surgical products.

Alginates are polysaccharide-like compounds extracted from certain sea weeds and have been described in great detail in numerous reports, literature, and patents (Kelco Algin, 2nd Ed., pgs 1–50, Kelco Co., Chicago Ill. 60606; Alginates in Pharmaceuticals and Cosmetics, Alginate Industries, Ltd., London W.C.2, Great Britain; Properties of Alginates, R. H. McDowell, Alginate Industries, Ltd., London, England, 1955; Alginates and Alginate Fibers in Clinical Practice, George H. Scherr, Wounds, Vol. 4, No. 2, 1992; U.S. Pat. Nos. 1,778,688; 1,814,981; 1,814,986; 2,477,861; and others.

One of the salient attributes of alginates is their ability to form gels when they react with certain polyvalant cations. Thus sodium alginate solutions which are soluble in water and other aqueous media will form gels when reacted with certain polyvalant ions which include calcium, zinc, aluminum, copper, and silver. The formation of alginate gels have been described in the literature and in patents (Kelco, ibid; U.S. Pat. Nos. 2,420,308; 3,349,079 and 3,386,921). The polyvalant ion-alginate gels so formed, such as calcium alginate, are insoluble in water but will dissolve in solutions of sodium salts of organic acids such as sodium hexametaphosphate, sodium glycero-phosphate, or sodium citrate.

The present invention utilizes alginates which are precipitated in a solution of a polyvalant ion such as calcium or zinc resulting in an aqueous insoluble product that could have utility in the fields of medicine, dentistry, or surgery when formed into bandages, dressings, or implants.

A study describing the use of absorbable alginate fiber dressings in the use of surgery was made by Blaine (George Blaine, Experimental Observations on Absorbable Alginate Products in Surgery, Annals of Surgery, January, 1947; pp 102–114). Alginate fibers and films were shown by Blaine to enhance the rate of healing in experimental animals as contrasted with controls.

Fairbairn and Whittet (J. W. Fairbairn and T. D. Whittet, Absorbable Haemostatics: Their Uses and Identification, The Pharmaceutical Journal, Feb. 28, 1948; pp 149–150), and Oliver & Blaine (British J. of Surgery, 37:1–4, 1950), reported that alginate fibers when used as absorbable hemostatic agents had significant advantages over oxidized cellulose in that oxidized cellulose inactivated penicillin whereas alginate did not and also that oxidized cellulose could not be sterilized by heat whereas alginate fibers could readily be sterilized by heat without their being significantly altered in physical and chemical characteristics.

Additional reports of the hemostatic properties of alginates have been made by Gosset (Texte de la communication faite le 16 mars 1949, a l'Academie de Chirurgie de Paris, Hopitaux de Paris; Twenty-Five Dental Cases Treated With Absorbable Alginate Wool, J. F. S. Rumble, British Dental Journal, Vol. LXXXVI, No. 8, 1949; A New and Effective Haemostatic Agent, Clifton A. H. Smith, Science, Vol. 103, No. 2681, Pg 634, 1946; Results With Alginate Materials in the Casualty Department of the Croydon General Hospital, Clarice Bray, Croydon General Hospital, Croydon, U.K.; Oral Use of Absorbable Alginate Derivatives to Arrest and Prevent Postextraction Hemorrhage, L. J. Allen, Oral Surgery, Oral Medicine, and Oral Pathology, Vol. 6, No. 2, pp 336–338, 1953;New Surgical Absorbable Hemostatic Agent, E. S. Hurwitt, et al., American Journal of Surgery, Vol. 100, 1960.

U.S. Pat. No. 3,853,383 describes a water-absorbant and water-disintegrative algin sponge prepared from alginic acid which may be utilized in medical or biological applications in which the alginate composition is quick frozen and then lyophylized resulting in an open cell porous alginate sponge product. The U.S. Pat. No. 3,853,383 utilizes a complex chemical procedure in which alginic acid is converted in part to calcium alginate and in part to sodium alginate after which all of this material has to be dried and pressed to remove alcohol and water and then milled in order to achieve a certain mesh size and the milled powder is then dissolved in water and blended at very high speed after which it is placed in a tray and lyophilized. (Although the U.S. Pat. No. 3,653,383 characterizes the mixture of calcium alginate and sodium alginate as being soluble (dissolved) in water prior to its being blended, calcium alginate is insoluble in water and it is not clear how such solution takes place as claimed in this patent. Although the abstract of the patent and the summary of the invention all set forth that the algin sponge so prepared is both water absorbent and water disintegrative, it is noted that all of the claims indicate that the calcium alginate component of the sponge is water insoluble; consequently a water insoluble alginate would not be expected to disintegrate in water).

U.S. Pat. No. 4,948,575 describes an alginate hydrogel foam wound dressing in which the sodium alginate solution, calcium containing insolubilizing solution, and foammaking chemicals are used in situ. Thus, all the chemical reactions take place at the site of and in the wound and lacks the capability of being stored as a dressing in a sterile form and made immediately available for use when required.

Alginates can be fabricated in a wide variety of compositions and are isolated from various species of seaweeds. It is noteworthy that the various alginates are composed of mannuronic acid and guluronic acid in various proportions. It has been shown that the relative proportion of mannuronic acid and guluronic acid may vary depending upon the species of seaweed from which they are extracted. Thus, the mannuronic acid content of alginate isolated from *Macrocystis pyrifera* is approximately 61% to 39% for guluronic acid whereas the mannuronic acid content of alginate isolated from *Laminaria hyperborea* is 31% to 69% for guluronic acid. Those alginates that have a high percentage of guluronic acid form rigid or brittle gels, whereas the alginates isolated from *Macrocystis pyrifera* contain a higher percentage of mannuronic acid and form elastic gels which can be deformed.

It is well known that the addition of calcium ions or in fact other earth metal ions such as zinc, aluminum, silver, or copper will precipitate alginate in the form of the metal ion alginate aqueous insoluble form. It is frequently desirable to prepare calcium alginate gels in certain physical forms. In order to achieve that, the precipitate of the calcium or other earth metal ion insoluble alginate has to be sequestered in order to permit the solution to be poured into a mold or a form and gelation take place after a suitable period of time so that the insoluble alginate gel will retain the form of the mold into which it is poured. Consequently, sequestering agents may be utilized such as ethylene, diamine, tetraacetic acid (EDTA) or sodium citrate (citric acid, trisodium salt dihydrate) in which the sequestering agent retards the precipitation of the insoluble metal ion alginate gel for a period of time that permits the sodium alginate and $Ca^{++}$ ion containing solution to be poured into a mold. Another method which has been utilized is to use an insoluble calcium salt such as calcium carbonate and by adding such an insoluble calcium salt to a solution of sodium alginate, which is then poured into a gel, the calcium ion reacts very slowly with the alginate moiety and consequently, precipitation of the calcium alginate gel is detained for an extended period of time, prior to gelation taking place in a suitable mold or container.

Alginate products when prepared as dressings, bandages, or implants, may require varying rates of disintegration in tissues depending upon the purpose for which they are to be used. It is one of the aspects of this invention that alginate products may be prepared having varying rates of disintegration in or on tissues depending upon specific needs. For example, bandages may be utilized as hemostats or dressings to cover exudating or nonexudating wounds or burns. Such dressings should retain their integrity for at least one to two weeks during which period the dressing may be lifted to examine the progress of a wound and, when desired, the dressing can be readily removed and a fresh dressing replaced thereon. Were the dressing to disintegrate very quickly in or on an exudating wound, then removal of the alginate dressing, which frequently disintegrates into a gelatinous amorphous entity, would be extremely difficult. On the other hand, were the alginate product formed for utilization as an implant which would have to retain its integrity for a few months or more, then it would be necessary to ensure that the product did not disintegrate in situ prior to the required time of its action. The capability inherent in our invention to alter the rates of alginate disintegration may principally be achieved by two methods:

Method A

The alginate composition is mixed with reagents and/or polymers which become coercive to the alginate molecule when the composition is so introduced into a calcium chloride solution, resulting in a precipitate and so entrapping the total composition. If the reagents or polymers other than that of alginate which are used have a high resistance to enzymatic and/or aqueous deterioration in tissues, then the time of retention of the integrity of the alginate product so prepared will be prolonged. Whereas, if the proportion of such an aqueous insoluble or enzyme-resistant polymer which becomes an integral micelle in the polymer network of the calcium alginate gel is thus reduced, then the time of dissolution of the alginate composition is shortened.

Method B

A solution of sodium alginate is mixed with calcium ions which are concomitantly mixed with a cross-linking agent to the sodium alginate where the cross-linking agent is resistant to aqueous and/or enzymatic deterioration in tissues. Thus for example, by altering the proportion of the calcium alginate left free as an insoluble gel and the calcium alginate which has been cross-linked to an insoluble moiety thus rendering it less susceptible to deterioration in aqueous tissues and/or resistant to enzymatic breakdown in tissues, then by thus adjusting the proportions of these two compounds, the rate of dissolution of this molecular complex could thereby be altered. The alteration of the rate of dissolution of such an alginate-cross-linked complex would result in an alteration in the rate of dissolution of the alginate dressing or implant in or on tissues.

Having set forth the tenets of the invention contained herein, the following non-limiting examples illustrate various compositions that are inherent in our invention:

EXAMPLE 1

Twenty ml of a 3.0% solution of Kelco sodium alginate XL-F is added to 12 ml of 2.0% sodium citrate as sodium citrate $0.6H_2O$.

The mixture is stirred and to it is added 0.5 ml of glycerin and 0.15 ml of surface active agent encoded L64, polyal BASF by Wyandotte Corp. After the composition has been stirred, 6 ml of 2% calcium chloride as calcium chloride $0.2H_2O$ is added slowly with vigorous stirring and when thoroughly mixed, the total composition is poured into a plate, dish or similar container. The liquid mixture of sodium alginate will gel in approximately 30 to 60 seconds after which time the plate or dish containing the gelled calcium alginate mixture is then quickly frozen, either in a freezer, dry ice chest, or liquid nitrogen.

The sodium citrate acts as a sequestering agent and delays immediate precipitation of the calcium alginate which otherwise would result in an incoherent number of insoluble calcium alginate globules.

After the dish containing the alginate mixture has been suitably frozen, it is inserted into a vacuum chamber, during which time lyophilization proceeds under vacuum until the moisture has been withdrawn. The resulting composition is a microporous dressing having excellent uniformity and being composed of calcium alginate.

EXAMPLE 2

Add 37.5 ml of a 3.0% solution of Kelco sodium alginate XL-F to 15.0 ml of a 2.0% solution of sodium citrate as sodium citrate $0.6H_2O$.

The mixture is stirred and to it is added 150 mg of porcine collagen dispersed as a colloidal dispersion in 10 ml of solution. To this mixture is added 0.5 ml of glycerin and 0.15 ml of the L-64 surface active agent. After the composition has been stirreds 7.0 ml of 2% calcium chloride as calcium chloride $0.2H_2O$ is added slowly with vigorous stirring, and when thoroughly mixed, the total composition is poured into a plate, dish, or similar container. After gelation has occured, the dish containing the gelled calcium alginate-collagen mixture is then quickly frozen either in a freezer, ice chest or liquid nitrogen.

As in Example 1, the sodium citrate acts as a sequestering agent and delays immediate precipitation of calcium alginate.

The dish containing the mixture which has been frozen, is then inserted into a vacuum chamber and lyophilized as described in Example 1.

This composition couples the unique advantages of calcium alginate as well as collagen for use in dressings that would act as a hemostat and in the reduction of bleeding time as well as forming a hydrocolloidal gel which has been shown to enhance the healing process when such dressings are utilized.

EXAMPLE 3

The zinc salt of bacitracin, having a concentration of 67 IU/mg, is added in an amount of 230 mg to 10 ml of deionized water. Neomycin sulphate powder assaying as 704 mog neomycin/mg of material is added to 10 ml of deionized water in an amount of 135 mg. Polymyxin B sulphate containing 8547 units of polymyxin B/mg of powder is added to 10 ml of deionized water in an amount of 22.6 mg.

The three separate solutions are stirred until all of the antibiotics have been dissolved and then they are mixed, to form a total of 30 ml of solution. To the antibiotic mixture is slowly added 30.0 ml of 5.0% sodium alginate XL-F and 0.5 ml of glycerin as well as 0.15 ml of L64 surface active agent.

The total solution is initially slowly stirred and then vigorously mixed while adding drop wise a mixture of 3.0 ml of a 2.0% solution of calcium chloride as calcium chloride $0.2H_2O$ and 12.0 ml of 2.0% sodium citrate as sodium citrate $0.6H_2O$.

The total solution is then poured into a dish, and after gelation has occurred, the dish is quick frozen either in a freezer, dry ice chest, or liquid nitrogen following which lyophilization takes place as described in Example 1 above.

EXAMPLE 4

Sodium alginate having a viscosity in aqueous solution of 170 centepoise at 2.0% concentration is dissolved in 100 ml of deionized or distilled water at a concentration of 2.0%. This solution also contains the following ingredients at final concentrations as indicated:

| | |
|---|---|
| A surface active agent-dioctyl derivative of succinic acid (aerosol OT-B) | 50 mg |
| Vegetable oil (Coconut oil) | 0.15 ml |
| Glycerin | 0.2 ml |
| A surface active agent (Tween 80) | 0.1 ml |
| Polyvinyl pyrolidine (PVP, 360,000 M.W.) | 50 mg |

This mixture is stirred with a magnetic stirrer until all of the reagents have been mixed.

To a solution of 12.0 ml of 2.5% calcium chloride as calcium chloride $0.2H_2O$ is added 2.0 grams of sodium citrate as sodium citrate $0.6H_2O$. The calcium chloride-sodium citrate solution is thoroughly mixed until all ingredients are dissolved and this solution is added to the alginate mixture prepared above with vigorous stirring and immediately following, the total composition is poured into a dish or plate, frozen and lyophilized as set forth in Example 1 above.

EXAMPLE 5

The sodium alginate solution described in Example 4 above is prepared and this alginate solution also now contains the following at the final concentrations shown:

| | |
|---|---|
| A surface active agent-dioctyl derivative of succinic acid (aerosol OT-B) | 150 mg |
| Glycerin | 3.0 ml |
| A surface active agent (Tween 80) | 0.1 ml |
| A carboxylated styrene butadiene copolymer latex (Encoded 68-412 by the Reichhold Chemical Co.) | 0.5 ml |

Twenty ml of a 3.0% solution of Kelco sodium alginate XL-F is added to 12 ml of 2.0% sodium citrate as sodium citrate $0.6H_2O$.

The sodium citrate acts as a sequestering agent and delays immediate precipiation of calcium alginate which otherwise would result in an incoherent number of insoluble calcium alginate globules.

The mixture is stirred and to it is added 0.5 ml of glycerin and 0.15 ml of L64 surface active agent. After the above composition has been stirred, slowly add a mixture containing 6 ml of 2% calcium chloride as calcium chloride $0.2H_2O$ and 12 ml of 2.0% sodium citrate as sodium citrate $0.6H_2O$ with vigorous stirring and when thoroughly mixed, the total composition is poured into a plate, dish or similar container. The mixture containing calcium alginate will gel in approximately 30 to 60 seconds, after which time the plate or dish containing the gelled calcium alginate mixture is then quickly frozen, either in a freezer, dry ice chest or liquid nitrogen following which lyophilization takes place as described in Example 1 above.

EXAMPLE 6

Sodium alginate having a viscosity as described in Example 4 is dissolved in 100 ml of deionized or distilled water to a final concentration of 2.0%. This solution also contains the following ingredients at final concentrations as indicated:

| | |
|---|---|
| A surface active agent-dioctyl derivative of succinic acid (aerosol OT-B) | 150 mg |
| Glycerin | 3.0 ml |
| A surface active agent (Tween 80) | 0.1 ml |
| A carboxylated styrene butadiene copolymer latex (encoded 68-412 by the Reichhold Chemical Co.) | 0.5 ml |
| A melamine-formaldehyde condensate (Encoded M-3 by American Cyanamid Co.) | 5.0 ml |

The mixture is stirred as described in Example 4.

To a solution of 20 ml of 2.5% calcium chloride as calcium chloride $0.2H_2$ O is added 1.0 gram of sodium citrate as sodium citrate $0.6H_2O$. The calcium chloride-sodium citrate solution is thoroughly mixed until the ingredients are dissolved and to it is added an amount of ammonium chloride to yield a final concentration of 5.0% of ammonium chloride. The calcium chloride-sodium citrate-ammonium chloride solution is added to the alginate mixture prepared above with vigorous mixing until a homogenous dispersion occurs and it is immediately poured into a dish, or plate, frozen, and lyophilized as set forth in Example 1 above.

EXAMPLE 7

A solution of sodium alginate is prepared as described in Example 4 above. This solution also contains the following ingredients at final concentrations as indicated:

| | |
|---|---|
| Glycerin | 3.0 ml |
| A surface active agent (Tween 80) | .75 ml |
| A carboxylated styrene butadiene copolymer latex (Encoded 68-412 by the Reichhold Chemical Co.) | 0.5 ml |
| A melamine-formaldehyde crosslinking agent (Encoded M-3 by American Cyanamid Co.) | 5.0 ml |
| Alkanolamine hydrochloride (20%) | 1.0 ml |

To a solution of 20 ml of 2.5% calcium chloride as calcium chloride $0.2H_2O$ is added 1.0 gram of sodium citrate as sodium citrate $0.6H_2O$. The calcium chloride-sodium citrate solution is throughly mixed until all ingredients are dissolved and this solution is added to the alginate mixture prepared above with vigorous stirring and immediately following, the total composition is poured into a dish or plate, frozen and lyophilized as set forth in Example 1 above.

EXAMPLE 8

Sodium alginate having a viscosity in aqueous solution of 170 centepoise at 2.0% concentration is dissolved in 100 ml of deionized or distilled water at a final concentration of 2.0%. This solution also contains the following ingredients at final concentrations as indicated:

| | |
|---|---|
| Glycerin | 3.0 ml |
| A surface active agent (Tween 80) | .75 ml |
| A carboxylated styrene butadiene copolymer latex (Encoded 40-438 by the Reichhold Chemical Co.) | 1.0 ml |
| A melamine-formaldehyde crosslinking agent (Encoded 3730 by American Cyanamid Co.) | 0.2 ml |
| Coconut oil | 0.2 ml |
| A surface active agent (Encoded Pluronic L64 (Polyal BASF by Wyandotte Corp.) | 0.2 ml |
| Polyethylene glycol 5% aqueous solution | 1.0 ml |
| An anionic water dispersed micro particle wax dispersion (labeled MICHEM Lube 270 by Michelman, Inc.) | 1.0 ml |

To a solution of 20 ml of 2.5% calcium chloride as calcium chloride $0.2H_2O$ is added 1.0 gram of sodium citrate as sodium citrate $0.6H_2O$. The calcium chloride-sodium citrate solution is thoroughly mixed until the ingredients are dissolved and this solution is added to the alginate mixture prepared above with vigorous stirring and immediately following, the total composition is poured into a dish or plate, frozen and lyophilized as set forth in Example 1 above.

EXAMPLE 9

Sodium alginate having a viscosity in aqueous solution of 170 centepoise at 2.0% concentration is dissolved in 100 ml of deionized or distilled water at a final concentration of 2.0%. This solution also contains the following ingredients at final concentrations as indicated:

| | |
|---|---|
| Glycerin | 3.0 ml |
| A surface active agent (Tween 80) | .75 ml |
| A surface active agent-dioctyl derivative of succinic acid (aerosol OT-B) | 50 mg |
| Coconut oil | 0.8 ml |
| An anionic water dispersed micro particle wax dispersion (labeled MICHEM Lube 270 by Michelman, Inc. | 5.0 ml |
| Polyvinyl alcohol (PVA 124,000 M.W.) | 0.2% |

To a solution of 20 ml of 2.5% calcium chloride as calcium chloride $0.2H_2O$ is added 1.0 gram of sodium citrate as sodium citrate $0.6H_2O$. The calcium chloride-sodium citrate solution is thoroughly mixed until the ingredients are dissolved and this solution is added to the alginate mixture prepared above with vigorous stirring and immediately following, the total composition is poured into a dish or plate, frozen and lyophilized as set forth in Example 1 above.

The above descriptions and examples illustrate particular constructions including the preferred embodiments of the solutions. However, the invention is not limited to the precise constructions described herein, but, rather, all modifications and improvements thereof encompassed within the scope of the invention.

The alginate principally utilized in the examples described herein was one having an aqueous viscosity of 170 centepoise at 2.0% concentration. It is clear that other alginates having other viscosities may be utilized without deviating from the novelty of the revelations contained in this patent as long as the alginate is of a concentration and viscosity that can be reasonably poured into a mold when a calcium or other anion alginate precipitating molecule is added to the sodium alginate. The alginate that we have principally used in the example described herein was sodium alginate, but it is clear that other water soluble alginates may be utilized without deviating from the novelty of the invention described herein such as water soluble ammonium alginate, magnesium alginate, or potassium alginate.

It is well known in the profession that various glycols as plasticizers may be used to improve the flexibility of alginate films or fibers. The plasticizer that we have principally used in the examples described herein has been glycerine because of its low cost and because of its ready availability. It is clear however that other plasticizers may be utilized such as propylene glycol, or ethylene glycol without deviating from the novelty of the invention described herein.

In the example cited, we utilized sodium citrate as a sequestering agent for the calcium ion in order that the aqueous insoluble calcium alginate moiety not precipitate during the preliminary mixing, but that precipitation of calcium alginate is postponed for a suitable period of time to permit the mixture to be poured into a suitable mold or tray. However, sequestering agents other than sodium citrate may be utilized without deviating from the novelty of the invention described herein such as ethylenediamine tetra-acetic acid (EDTA).

In the examples cited herein, calcium chloride has been utilized to provide the calcium ion which precipitates the insoluble calcium alginate which also may serve to entrap into the calcium alginate matrix other components as described herein. It is clear, as has been mentioned, that other salts may be utilized to precipitate the alginate such as those of aluminum, zinc, copper, chromium, or silver and these insoluble alginates may readily be utilized to precipitate the coercive alginate-polymer mixtures described in the Examples provided herein without deviating from the essential merits of this invention. However, since the alginate compositions are to be utilized in and on biological tissues, the particular salt utilized to precipitate the alginate should be dictated by any restraints of toxicity or other untoward reactions that might result from their use for the preparation of bandages, dressings, or surgical products as herein described.

Note that in example 2, we utilized collagen as a component in the alginate mixture so that the insoluble calcium alginate gel will contain an agent which has hemostatic activity and therefore would serve to stem the flow of blood from a wound when a dressing containing collagen is placed thereon. However, it is clear that other medicinal agents may be incorporated into the sodium alginate mixture prior to its being precipitated as a sodium alginate gel which medicinal agents serve to treat a wound by slowing being released from the insoluble calcium alginate moiety either by osmosis or by the gradual slow dissolution of the calcium alginate gel, and such medicinal agents can be incorporated into the mixture without deviating from the novelty of the invention described herein, such as anti-inflammatory agents, antibiotics, and anti-bacterial agents.

Many of the examples described herein utilize the surface active agents such as those characterized as Tween 80, aerosol OT-B, or Pluronic L64. These surface-active agents are utilized primarily to effect a dispersion between the non-aqueous miscible components utilized in achieving a coercive mixture with the aqueous soluble sodium alginate in order to insure a homogenuity throughout the solutions that are then precipitated as insoluble alginate compositions.

These surface active agents are also utilized in order to improve the wetting of a medical dressing or bandage in the event that a wound may be exudating, and the enhanced wioking in such a bandage or medical dressing serves to quickly absorb any blood or serum from a wound.

It is clear that other surface active agents may be used for these purposes without deviating from the novelty of the invention described herein.

In order to enhance the retention of our alginate gelled composition in or on tissues, we have prepared either as coacervates or covalently linked substances which would tend to enhance the insoluble property of the calcium alginate moiety for extended periods of time by utilizing agents such as stytens butadiene copolymer latex or a melamine-formaldehyde condensate or a wax micro particle dispersion as set forth in the examples. However, it is clear that other insoluble moieties may be utilised as coacervates or covalently linked to the alginate molecule which would serve to enhance the longevity in tissues of the dressing or implants so utilized without deviating from the novelty from the invention described herein.

I claim:

1. A method of making a water-insoluble alginate sponge or foam product to be utilized in the preparation of wound dressings or surgical products comprising the steps of:
   (I) mixing together, to form a composite liquid mixture, a first liquid mixture comprising:
      (a) an aqueous solution of a water soluble alginate composition with a water soluble sequestering agent;
   (II) adding to the mixture (I) a plasticizer and a surface active agent;
   (III) while allowing the total composition of (I) and (II) to be mixed vigorously, adding a di- or trivalent metal ion capable of complexing the water-soluble alginate to form water-insoluble alginate hydrogels;
   (IV) pouring said composite liquid mixture into a dish or tray until the water-insoluble alginate hydrogel forms;
   (V) placing said insoluble alginate hydrogel form contained in a tray or dish into a freezer until the composite insoluble alginate hydrogel is frozen;
   (VI) lyophilizing said frozen composite insoluble alginate hydrogel until all of the moisture has been removed.

2. A method of making a water-insoluble alginate sponge or foam product to be utilized in the preparation of wound dressings or surgical products comprising the steps of:
   (I) mixing together, to form a composite liquid mixture, a first liquid mixture comprising:
      (a) an aqueous solution of a water soluble alginate composition with a water soluble sequestering agent;
   (II) adding to the mixture (I) a plasticizer, a surface active agent, and a suitable medicinal agent for the treatment of wounds;
   (III) while allowing the total composition of (I) and (II) to be mixed vigorously, adding a di- or trivalent metal ion capable of complexing the water-soluble alginate to form water-insoluble alginate hydrogels;
   (IV) pouring said composite liquid mixture into a dish or tray until the water-insoluble alginate hydrogel forms;
   (V) placing said insoluble alginate hydrogel form contained in a tray or dish into a freezer until the composite insoluble alginate hydrogel is frozen;
   (VI) lyophilizing said frozen composite insoluble alginate hydrogel until all of the moisture has been removed.

3. A method of making a water-insoluble alginate sponge or foam product to be utilized in the preparation of wound dressings or surgical products comprising the steps of:
   (I) mixing together, to form a composite liquid mixture, a first liquid mixture comprising:
      (a) an aqueous solution of a water soluble alginate composition with a water soluble sequestering agent;
   (II) adding to the mixture (I) a plasticizer, a surface active agent, and an aqueous insoluble agent that can form a coacervate with a water-insoluble alginate hydrogel;
   (III) while allowing the total composition of (I) and (II) to be mixed vigorously, adding a di- or trivalent metal ion capable of complexing the water-soluble alginate to form water-insoluble alginate hydrogels;
   (IV) pouring said composite liquid mixture into a dish or tray until the water-insoluble alginate hydrogel forms;
   (V) placing said insoluble alginate hydrogel form contained in a tray or dish into a freezer until the composite insoluble alginate hydrogel is frozen;
   (VI) lyophilizing said frozen composite insoluble alginate hydrogel until all of the moisture has been removed.

4. A method of making a water-insoluble alginate sponge or foam product to be utilized in the preparation of wound dressings or surgical products comprising the steps of:
   (I) mixing together, to form a composite liquid mixture, a first liquid mixture comprising:
      (a) an aqueous solution of a water soluble alginate composition with a water soluble sequestering agent;
   (II) adding to the mixture (I) a plasticizer, a surface active agent, and a water soluble agent than can chemically cross-link with the alginate moiety to form an aqueous-insoluble complex;
   (III) while allowing the total composition of (I) and (II) to be mixed vigorously, adding a di- or trivalent metal ion capable of complexing the water-soluble alginate to form water-insoluble alginate hydrogels;
   (IV) pouring said composite liquid mixture into a dish or tray until the water-insoluble alginate hydrogel forms;
   (V) placing said insoluble alginate hydrogel form contained in a tray or dish into a freezer until the composite insoluble alginate hydrogel is frozen;
   (VI) lyophilizing said frozen composite insoluble alginate hydrogel until all of the moisture has been removed.

5. The method of making a water-insoluble alginate sponge or foam product as recited in claim 1 wherein said water-soluble alginate is selected from a group consisting of ammonium, magnesium, potassium, and sodium salts of alginate.

6. The method of making a water-insoluble alginate sponge or foam product as recited in claim 1, wherein said di- or trivalent metal salt is selected from a group consisting of calcium, zinc, aluminum, copper, chromium, or silver.

7. The method of making a water-insoluble alginate sponge or foam product as recited in claim 1, wherein said surface active agent is selected from a group consisting of Tween 80, Aerosol O-TV or pluronic L64.

8. The method of making a water-insoluble alginate sponge or foam product as recited in claim 1, wherein said plasticizer is selected from a group consisting of sodium citrate, ethylenediamine tetra-acetic acid.

9. The method of making a water-insoluble alginate sponge or foam product as recited in claim 2, wherein said suitable medicinal agent is selected from a group consisting of antibiotics, collagen, antimicrobial agents, and anti-inflammatory agents.

10. The method of making a water-insoluble alginate sponge or foam product as recited in claim 3, wherein said aqueous insoluble agent that can form a coacervate with a water-insoluble alginate hydrogel is selected from a group consisting of waxes, lipids, and latex particles.

11. The method of making a water-insoluble aginate sponge or foam product as recited in claim 4, whereas said water soluble agent that can chemically cross-link with the alginate moiety is selected from a group consisting of melamine formaldehyde cross-linking agent.

12. A water-insoluble alginate sponge or foam wound dressing prepared by the method of claim 1.

13. A water-insoluble alginate sponge or foam wound dressing prepared by the method of claim 2.

14. A water-insoluble alginate sponge or foam wound dressing prepared by the method of claim 3.

15. A water-insoluble alginate sponge or foam wound dressing prepared by the method of claim 4.

16. A water-insoluble alginate sponge or foam wound dressing prepared by the method of claim 5.

17. A water-insoluble alginate sponge or foam wound dressing prepared by the method of claim 6.

18. A water-insoluble alginate sponge or foam wound dressing prepared by the method of claim 7.

19. A water-insoluble alginate sponge or foam wound dressing prepared by the method of claim 8.

20. A water-insoluble alginate sponge or foam wound dressing prepared by the method of claim 9.

21. A water-insoluble alginate sponge or foam wound dressing prepared by the method of claim 10.

22. A water-insoluble alginate sponge or foam wound dressing prepared by the method of claim 11.

\* \* \* \* \*